United States Patent [19]

Miller et al.

[11] 4,454,877

[45] Jun. 19, 1984

[54] PORTABLE NEBULIZER OR MIST PRODUCING DEVICE

[75] Inventors: Jack V. Miller, Sierra Madre; Stephen T. Blosser, San Gabriel, both of Calif.

[73] Assignees: Andrew Boettner; Mrs. Andrew Boettner, both of Newport Beach, Calif.

[21] Appl. No.: 287,544

[22] PCT Filed: May 26, 1981

[86] PCT No.: PCT/US81/00709

§ 371 Date: May 26, 1981

§ 102(e) Date: May 26, 1981

[87] PCT Pub. No.: WO82/04193

PCT Pub. Date: Dec. 9, 1982

[51] Int. Cl.³ .............................................. A61M 15/00
[52] U.S. Cl. ........................... 128/200.21; 128/200.23; 128/202.13; 128/203.14
[58] Field of Search ................. 128/200.14, 200.18, 128/200.21, 200.23, 202.13, 202.16, 203.12, 203.21, 203.23, 203.25, 203.29, 204.13, 205.21, 200.28, 200.24; 222/415, 187, 5; 261/78 A, 104, DIG. 65, 99, 76, 95; 239/289, 44, 145, 338, 308, 346, 366

[56] References Cited

U.S. PATENT DOCUMENTS

| 1,144,719 | 6/1915 | Melas | 261/76 |
| 1,771,366 | 7/1930 | Wyss et al. | 128/204.13 |
| 2,181,421 | 11/1939 | Fahr et al. | 128/200.21 |
| 2,442,648 | 6/1948 | Goldman | 222/5 |
| 2,665,943 | 1/1954 | Palm | 239/366 |
| 2,847,006 | 8/1958 | Griffith | 128/202.13 |
| 3,119,561 | 1/1964 | Wilson | 239/308 |
| 3,658,059 | 4/1972 | Steil | 128/200.21 |
| 3,762,409 | 10/1973 | Lester | 128/200.14 |
| 3,983,869 | 10/1976 | Suzuki | 261/95 |
| 4,116,387 | 9/1978 | Kremer, Jr. et al. | 128/200.18 X |
| 4,161,282 | 7/1979 | Erb et al. | 128/200.14 |

FOREIGN PATENT DOCUMENTS

| 545607 | 3/1956 | Belgium | 128/200.28 |
| 326142 | 9/1920 | Fed. Rep. of Germany | 261/99 |
| 82811 | 11/1953 | Norway | 261/99 |
| 8472 | 11/1897 | Sweden | 261/99 |
| 250920 | 7/1926 | United Kingdom | 239/308 |

Primary Examiner—Kyle L. Howell
Assistant Examiner—Christine A. Fukushima
Attorney, Agent, or Firm—Wagner & Bachand

[57] ABSTRACT

A nebulizer comprising of an elongated body including a nebulized fluid emission opening at one end with a nebulizer fluid reservoir communicating with the opening and a fluid barrier means adjacent to the opening. A wick extends between the reservoir and barrier for conveying nebulizer fluid to the barrier region from the reservoir. A source of pressurized gas is within a housing along with a means for conveying the pressurized gas to the wick in the region of the barrier. The conveying means includes a perforated section which extends into the region of the wick and through the barrier. The pressurized gas traverses the conducting means and aspirates the nebulizer fluid during passage through the barrier. The perforated section is a helical spring and the wick is a carpet-like fabric. A novel form of perforated barrier in the form of a closely spaced helical spring is enclosed. A novel filter formed from a knurled rod within a passage also is disclosed.

24 Claims, 9 Drawing Figures

U.S. Patent   Jun. 19, 1984   Sheet 1 of 3   4,454,877
Fig.1
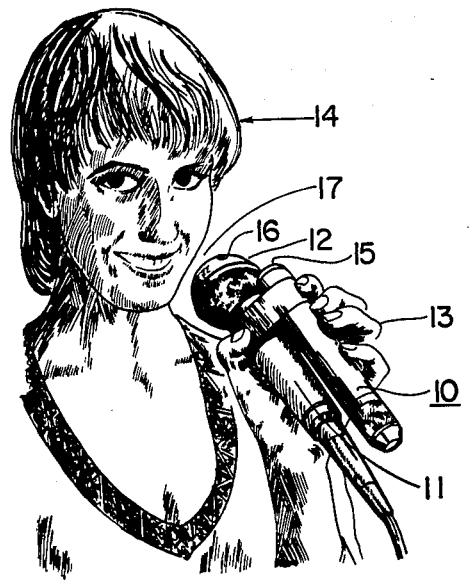
Fig.2
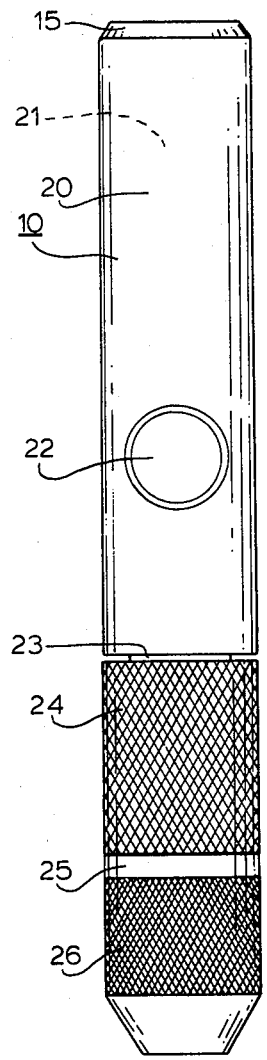
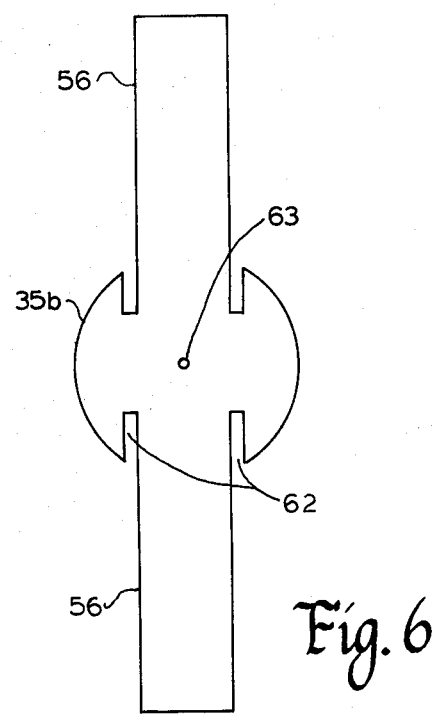
Fig.6

CO₂ FLOW

NO CO₂ FLOW

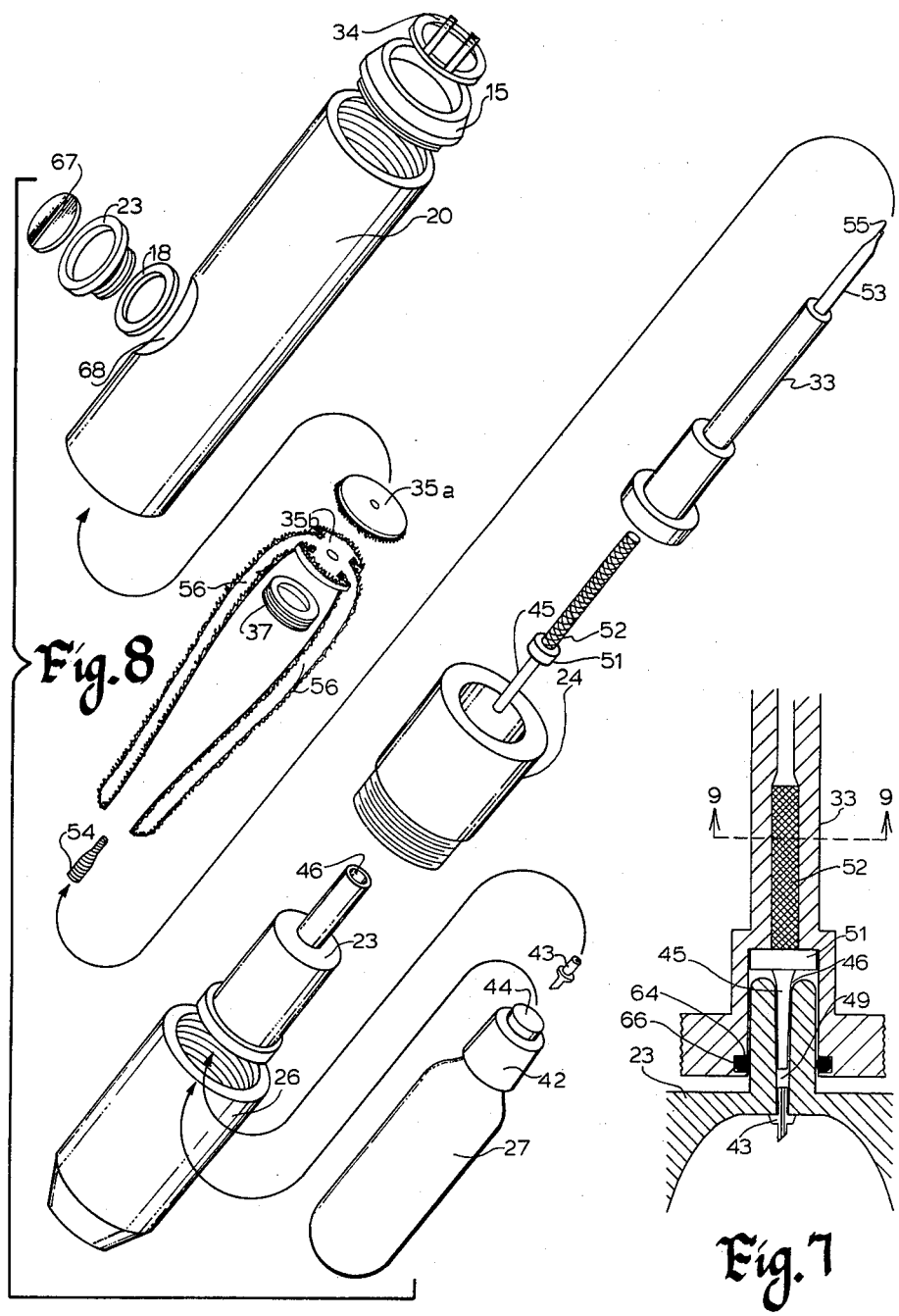

PORTABLE NEBULIZER OR MIST PRODUCING DEVICE

BRIEF DESCRIPTION OF THE INVENTION

Recognizing the need for a device to alter the moisture content of the air in the immediate area of the performer or speaker, we have designed a lightweight and convenient nebulizer or humidifier which attaches directly to a microphone by means of an attaching device such as a hook and loop fabric strap. The nebulizer is a small cylindrical shaped device which, because of its shape and light weight, goes almost unnoticed by the performer when attached to the microphone.

Noticeable to the performer is the soothing mist emitted by this device which enhances his or her vocal performance. Precise engineering of this minature humidifier causes pressurized carbon-dioxide ($CO_2$) to mix with distilled water and create a fog-like mist which is able to soothe the vocal chords. The density and quality of the fog-like mist is adjustable to meet the individual needs and preferences of all performers. This fog-like mist cannot be physically seen by the audience, cannot be detected by the sound system.

The carbon dioxide gas which serves as a nebulizer to the distilled water in this device also propels it outward to form a plume of moist air which is invisible except with strong back-liighting. The gas comes in a cartridge which powers the device from two to four hours depending on the setting of the mist control. The quantity of distilled water equals the carbon dioxide gas supply in that it will last from two to four hours, also depending upon the setting of the mist control. Refilling the water supply and changing the cartridge is a fast and easy procedure.

BRIEF DESCRIPTION OF THE DRAWINGS

This invention can be more clearly understood from the following detailed description and by references to the drawings in which:

FIG. 1 is a perspective view of an entertainer using the invention attached to a microphone;

FIG. 2 is a front and elevational view of the external features of this invention;

FIG. 6 is a top view of the absorbent fabric disk used in this invention;

FIG. 7 is an enlarged fragmentary longitudinal sectional view of the valve portion of this invention;

FIG. 8 is an exploded view of the invention; and

DETAILED DESCRIPTION OF THE INVENTION

Figure 5:
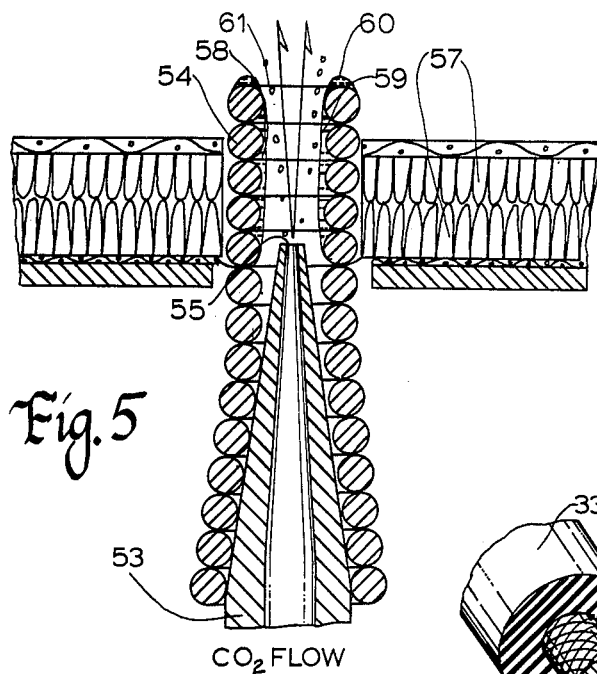
FIG. 5 is an even greater enlarged fragmentary longitudinal sectional view of the helical coil and absorbent disks forming the emitter portion of this invention.

Looking now to the detailed drawings in which in FIG. 1, one sees a perspective view of the nebulizer 10 is attached to the handle 11 of a microphone 12 and in use by an entertainer 14. This figure illustrates the relative size and positioning of the nebulizer 10 on the microphone handle 11. The hand 13 of the entertainer 14 comfortably fits around both the nebulizer 10 and the microphone handle 11.

The exact placement of the nebulizer 10 can vary with the personal preference of the individual performer although generally placement of this device is on the upper surface of the microphone handle 11 with the face cap 15 located slightly below the sensitive portion 16 of the microphone 12. When a cardiod microphone is used, the nebulizer is located as close to the null region at the rear of the microphone as possible. This positioning of the nebulizer 10 contributes to a more effective dispersion of the mist emitted by this device into the facial region 17 of a performer where it is needed.

Referring now to FIG. 2 which illustrates the external features of this device. The major portion of the nebulizer 10 is made up of a main body 20 which houses a distilled water reservoir 21 and various emitting elements all of which are shown in FIG. 3.

Somewhat centrally located on the main body 20 is a reservoir filler cap 22 which provides easy access to refill the reservoir 21 located within the main body 20. The nebulizer 10 uses only distilled or deionized water to insure that the mist emitted from this device is free from contaminants as well as to avoid clogging of the device due to particle build up.

Located on the anterior portion of the nebulizer 10 is a chrome face cap 15 which helps to protect the internal working elements of the emitter portion of the device. The chrome face cap 15 also serves to eliminate a small amount of side spray of the mist by directing the spray outward.

Directly adjacent to the main body 20 a small portion of an internal valve body 23 is seen. Next to the internal valve body 23 an external knurled valve body 24 is found. The external valve body 24 is knurled because rotation of this part opens and closes an internally located valve.

Manipulation of the external valve 24 allows the adjustment of the density and quality of the mist emitted from the nebulizer 10 due to the threaded relationship which exists between the nebulizer body 20 and the valve body 23. The knurled texture maintains a sure grip while rotating the valve body 24. A polished section 25 separates and identifies the external valve body 24 and a knurled end cap 26. The end cap 26 also is threaded to the external valve body 24.

The end cap 26 serves to hold a carbon dioxide ($CO_2$) cartridge or cylinder but is not involved in the adjustment of the mist emitted from the nebulizer 10. The end cap 26 is readily removed for a quick replacement of $CO_2$ cylinders when the old one is empty.

The operational relationship depicted in FIG. 2 is demonstrated in FIG. 3. The neck 40 of a $CO_2$ cylinder 27 rests in a cylinder recess 41 in the lower portion 31 of the internal valve body 23 and end cap 26. An annular gasket 42 encircles the neck 40 of the cylinder 27 and serves to insure a gas tight fit of the cylinder 27 in the recess 41. A cylinder piercing needle 43 is depicted piercing the cylinder top 44 thus allowing the pressurized $CO_2$ within the cylinder 27 to travel a pathway up into the main body 20 of the nebulizer 10.

The pathway which the $CO_2$ travels within the nebulizer 10 can be followed by referring to the dash-dotted line found in FIG. 7. $CO_2$ travels from the cylinder 27 through the cylinder piercing needle 43 through air space found between the tapered end 45 of the valve stem 32 and the tapered tubular opening 46 of the valve if open. The $CO_2$ then travels around the annular stop 51 and up, in a criss-cross pattern, through the knurled filter portion 52 of the valve stem 32. It is at this point that contaminants in the $CO_2$ are trapped by the filter 52. The available $CO_2$ cartridges are sufficiently contaminant free but the filter 52 provides further assurances of freedom from contamination.

The $CO_2$ after passing the knurled filter 52 progresses up the emitter tube or jet 53. Lastly, the $CO_2$ travels through a helical emitter coil 54 which rests in the tip 55 of the emitter tube 53. The helical emitter coil 54 extends through two pile fabrics, e.g. "Velcro" pile disks 35a and 35b and through the backing 36 of fabric disk 35a where the $CO_2$ is released out into the atmosphere. The emitted product from the nebulizer is not merely $CO_2$ but a fog-like mist which is able to increase the humidity in the air which an entertainer or speaker breathes when the nebulizer 10 is attached to a microphone. The change from $CO_2$ to a fog-like mist occurs in the nebulizer at the point where the $CO_2$ comes in contact with the distilled water which is used in this device 10.

Figure 3:
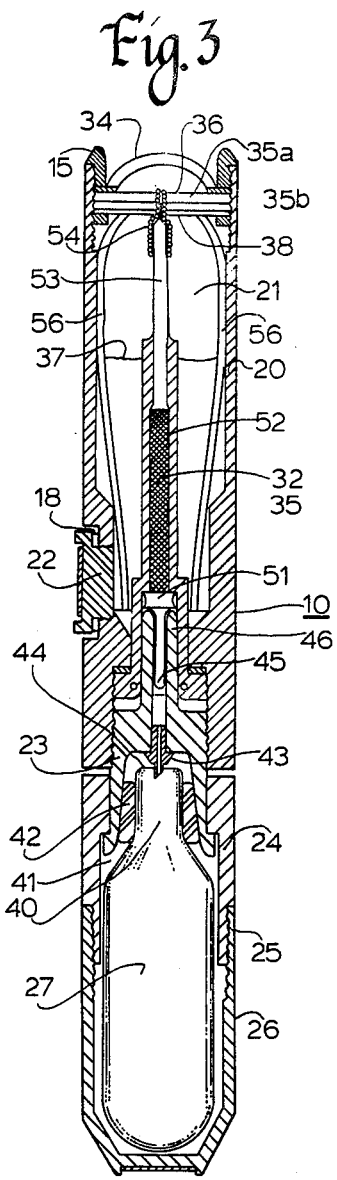
FIG. 3 is a longitudinal cross-sectional view of the invention showing the internal workings.

Distilled water is placed into the reservoir 21 by removal of the reservoir filler cap 22 and washer 65 and pouring the water into the reservoir 21. A typical water level 37 appears in FIG. 3. The end flaps 56 of the absorbent fabric disk 35b function as a wick and transports the distilled water in the reservoir 21, no matter what the water level is, up to the absorbent fabric disk 35a. The amount of $CO_2$ emitted and water carried depends upon the adjustment of valve 23.

Figure 4:
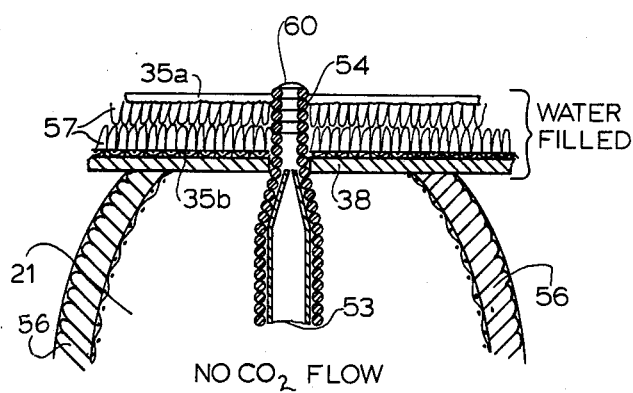
FIG. 4 is an enlarged fragmentary longitudinal sectional view of the emitter portion of this invention.

We refer now to FIG. 4 which enables a clear view of the parts involved in the conduction of the water from the reservoir 21 to be seen. The end flaps 56 of the absorbent fabric disk 35b are seen resting in the general area of the distilled water reservoir 21. (See FIG. 3.)

Due to the capillary action demonstrated by such absorbent fabrics as pile fabric, like Velcro, as is used in this invention, any level of distilled water in the reservoir will cause the absorbent legs 56 to transport water to the loops 57 of the Velcro fabric 35 where it is held in a thin sheet between the backing 36 between the backing of disk 35a and a support disk 38 due to the surface tension of water. Water molecules move from the loops 57 of the Velcro disks 35 to the outside and thence the inside of the helical emitter coil 54 and form a meniscus 60 due also to the surface tension of water. The interstices between the turns of the helix or coil 54 constitute perforations in the emitter wall.

FIG. 5 illustrates the nebulizer in operation with loops 57 of the loop pile disks 35 and the helical emitter coil 54 water filled with no meniscus 60. The inside diameter of emitter coil 54 is preferably 0.020–0.040 inches in diameter while coils of inside diameter of 0.01 to 0.05 inches will work. A stream of $CO_2$ is emitted from the nozzle 55, passes through the helical emitter coil 54 and forms an outlet 61 with an inside diameter in the order of 0.002 to 0.010 inches.

The nozzle 55 is in the order of 0.0015 and 0.002 inches in diameter providing high velocity quiet stream of gas into the larger diameter nebulizing restriction passage 61. The $CO_2$ passing thru the orifice 61 picks up the water molecules which fill the space between the turns of coil 54. The water lining is illustrated by lines 58 and 59 describing a hole through droplet 60. The distilled water and $CO_2$ mixture is dispersed out past the emitter quard 34 (shown in FIG. 3) in the form of a fog-like mist. Whenever the valve 24 is closed, $CO_2$ flow ceases and the meniscus 60 reforms.

Depicted in FIG. 6 is an absorbent fabric disk 35b with end flaps 56 which act as a wick in the nebulizer 10. Slits 62 in the absorbent fabric disk 35b allow the end flaps 56 to rest in the reservoir 21 seen in FIG. 3. A hole 63 in the center of the absorbent fabric disk 35b allows the extension of the helical emitter coil 54 through the disk like water holding fabric 35.

Referring now to FIG. 7, adjustment of the fog-like mist by rotation of the external valve body 24 not shown in this figure, changes the amount of space between the tapered end 45 of the valve stem 32 and the tapered tubular opening 46 which is located within the internal valve body 23. In this figure the valve is opened as evidenced by the presence of a space 47 which is seen between the internal valve body 23 and the annular stem stop 51 of the emitter body 33. The tapered end 45 of the valve stem inserts into the tapered tubular opening 46 and either opens or closes the pathway for the $CO_2$ to travel. Present on the lower end 40 of the emitter body 33 is a side wall recess 54 which houses an "O" ring seal 66. Providing a gas tight seal between the valve body 23 and the emitter body 33.

The valve stem 32 is made up of three sections, a tapered end 45, an annular stem stop 51 and a knurled filter 52 in "push fit" relationship within the recess in emitter body 33. The annular stem stop 51 secures the placement of the entire valve stem 32 with the emitter body 33. The novel knurled filter 52 provides a plurality of helical pathways for the $CO_2$ to travel up the emitter body 33 and also serves to trap contaminants which may be present within the system and could eventually seriously impede the flow of the mist from the nebulizer. The knurled filter 52 is easily cleaned by rinsing with distilled water thus allowing maintenance of this part to be relatively simple.

FIG. 8 is an exploded view of the invention which illustrates how the parts of this device fit together. Beginning with reservoir filling cap 23, gasket 18 and a "distilled water only" label 67 all fit together and thread in a filler opening 68 in the main body 20. The label 67 actually adheres to the top 70 of the reservoir cap 23. Threading into the upper portion of the main body 20 is an emitter guard 34 and a face cap 15. The emitter guard 34 protects the emitting parts of the nebulizer 10, namely the helical emitter coil 54 and the tip 55 of the emitter tube 53. The face cap 15 secures the guard 34 to the main body 20 and directs the mist outward. Adjacent to the emitter guard 34 are then placed, two Velcro disks 35a and 35b, the latter including end flaps 56. These water holding pieces are placed within the emitter body 20 next to the emitter guard and are backed by a threaded nut 37. The helical emitter coil 54 is pushed through openings in the nut 37 and disks 35a and 35b. The emitter tube 53 with its attached emitter body 33 receives the valve stem 32 within its internal recess shown in FIG. 3. The tapered end 45 of the valve stem 32 projects into the tapered tubular opening 46 of the internal valve body 23. The external valve body 24 fits over the portions of the emitter body 33 and the internal valve body 23. The cylinder piercing needle 43 is press fit into its recess in internal valve body 23.

Cylinder 27 is dropped into end cap 26 and cup 26 is threaded onto external valve body 24 until it brings the top 44 of the cylinder 27 into engagement with piercing needle 43. Prior to such engagement, throat gasket or seal 42 has engaged the wall of the internal valve body 23 to establish a gas tight seal. The cylinder remains in the nebulizer until fully discharged. Any attempt to release the cylinder before full discharge by unscrewing end cap 26 results in release of seal 42 before the end cap 26 threads disengages and all residual pressure is released via the thread clearances.

From the foregoing it should be clear that we have produced a truly portable nebulizer which is totally self contained. It supplies a mist-like fog generated by a harmless and inexpensive gas carried in its sealed cartridge. The nebulizer employs a novel liquid holding system at the emitter region, namely, pile fabric surrounding a helical emitter. A novel wicking system also which provides a continuous supply of water to the point of nebulization. The emitter itself is a simple but effective small diameter tube produced by closely spaced helical turns of wire which pass the nebulizing fluid between adjacent turns to provide a continuous supply of fluid. Nebulizing action is near instantaneous when opened, throttlable precisely and effectively stopped by closure of the throttling valve. The entire apparatus is unobtrusive and may be attached to conventional microphones without interferences with their operation.

Figure 9:
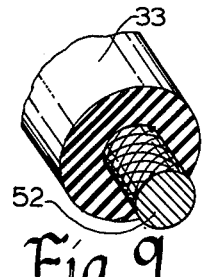
FIG. 9 is an enlarged, fragmentary perspective view of the knurled filter of this invention taken from the section labelled 9—9 of FIG. 7.

Referring now to FIG. 9, one may see the simple effective knurled filter 52 of this invention tightly fitted within the emitter body 33.

The above described embodiments of this invention are merely descriptive of its principles and are not to be considered limiting. The scope of this invention instead shall be determined from the scope of the following claims, including their equivalents.

What is claimed is:

1. A portable self-contained humidifier comprising:
   an elongated hand graspable body;
   said body including an outlet for the emission of nebulized water;
   said body including a reservoir for nebulizing fluid such as water;
   said body including a chamber for holding a source of nebulizing gas;
   means within said body for directing nebulizing gas through said reservoir to aspirate fluid therefrom and to convey the gas carried fluid out of said body through said outlet whereby a person may hold said body and direct a cloud of nebulized water into the region of his mouth to humidify his air breathed;
   including adjustable attachment means for securing said humidifier to the handle of a hand held microphone whereby said outlet is directed toward the holder's mouth and throat while the microphone is in use.

2. A portable self-contained humidifier comprising:
   an elongated hand graspable body;
   said body including an outlet for the emission of nebulized water;
   said body including a reservoir for nebulizing fluid such as water;
   said body including a chamber for holding a source of nebulizing gas;
   means within said body for directing nebulizing gas through said reservoir to aspirate fluid therefrom and to convey the gas carried fluid out of said body through said outlet whereby a person may hold said body and direct a cloud of nebulized water into the region of his mouth to humidify his air breathed;
   including a nebulizing fluid retainer surrounding said conduit means in the region of said outlet whereby nebulizing gas passing through said conduit means picks up nebulizing fluid from said retainer;
   including a helical spring defining said conduit means,
   said helical spring passing through said retainer whereby nebulizing fluid held by said retainer migrates through the turns of said helical spring and provides nebulizing fluid between the turns.

3. The combination in accordance with claim 2 wherein at least some of the turns of said helical spring turns are in contact with adjacent turns and the central opening of said helical spring is of such small diameter that nebulizing fluid such as water will fill the outlet thereof in the absence of gas flow therethrough.

4. The combination in accordance with claim 3 wherein the wire diameter in said helical spring is between 0.002 and 0.010 inches.

5. The combination in accordance with claim 3 including a gas passage from said source of nebulizing gas including an orifice discharging a flow of gas into the opening in said helical spring.

6. The combination in accordance with claim 5 wherein said orifice is between 0.0015 and 0.002 inches in diameter to provide a high velocity stream of gas into said helical spring.

7. The combination in accordance with claim 2 wherein said nebulizing fluid retainer comprises a pile fabric including a relatively fluid retaining backing, said retainer positioned with the pile side exposed to the reservoir and the backing exposed to the exterior of said body in the region of said outlet,
   the pile of said fluid retainer in fluid transfer relationship with the exterior of said helical spring.

8. The combination in accordance with claim 2 including wick means contained within said reservoir and extending into fluid transfer relationship with said fluid retainer.

9. The combination in accordance with claim 8 wherein
   said retainer comprises a pile fabric with the pile directed toward the interior of said body and
   said wick means comprises a pile fabric with a portion of the pile in contact with the pile of said fluid retainer.

10. The combination in accordance with claim 9 wherein said wick means includes a portion with the pile thereof in face-to-face relationship with the pile of said retainer and whereby a supply of nebulizing fluid is maintained in the region of said helical spring regardless of the attitude of the humidifier or the extent of fill of the reservoir.

11. A nebulizer comprising:
   an elongated body including a nebulized fluid emission opening at one end thereof;
   a nebulizer fluid reservoir therein communicating with said opening;
   a fluid retainer adjacent to said opening;
   a source of gas pressure within said body positioned remote from said opening; and
   means conveying gas pressure from said source of gas pressure through the region of said fluid retainer;
   said gas pressure conveying means including a perforate section extending into the region of said retainer;

whereby gas traversing said conveying means aspirates nebulizer fluid during passage through said fluid retainer;
wherein said perforated conveying means comprises a closely spaced helix.

12. The combination in accordance with claim 11 wherein said perforate conducting means comprises a helix of closely spaced wires defining an outlet in the range of 0.010 to 0.050 inches in diameter and said adjacent turns are at least partially in contact with each other in the region of said fluid reservoir.

13. The combination in accordance with claim 1 wherein said fluid retainer comprises a pile fabric surrounding said perforate section of said gas conveying means with at least part of the pile exposed to the nebulizer fluid within said reservoir.

14. The combination in accordance with claim 12 including wick means within said reservoir extending into liquid transfer relationship with said fluid retainer.

15. The combination in accordance with claim 14 wherein said perforate conducting means extends through said wick means in fluid transfer relationship therewith.

16. The combination in accordance with claim 14 wherein said wick means comprises a pile fabric having pile and a backing and said closely spaced helix traverses said fabric through the backing and pile thereof.

17. The combination in accordance with claim 14 wherein said wick means includes at least one leg extending downward into said reservoir and an enlarged central portion in the region of said opening.

18. The combination in accordance with claim 14 wherein said fluid retainer comprises a pile fabric with the backing exposed to the exterior of said body and the pile exposed to and in fluid transfer relationship with said wick means.

19. The combination in accordance with claim 18 wherein said fluid retainer and said wick means are both pile fabrics in opposed facing position defining a fluid retaining region therebetween.

20. The combination in accordance with claim 1 wherein said source of gas pressure comprises a replaceable cartridge and gas conveying means including means for piercing the cartridge and means defining a gas flow passage including an orifice discharging a stream of gas through said helical conveying means.

21. A nebulizing device for use with a source of gas pressure comprising:
a helical spring defining a restricted passage and an opening at each end thereof,
said helical spring communicating with a source of gas to provide a flow of gas through said restricted passage in the direction of the axis of said opening,
means conducting a liquid to the exterior of said helical spring whereby the liquid may flow through the interstices between turns of said helical spring to provide a nebulizing fluid within said restricted passage.

22. The combination in accordance with claim 21 in which the helical spring includes a tapered inlet portion and a relatively uniform diameter nebulizing fluid passage portion.

23. The combination in accordance with claim 21 wherein said opening is between 0.010 and 0.050 inches in diameter.

24. A nebulizing device for use with a source of gas pressure comprising:
a helical spring defining a restricted passage and an opening,
said helical spring communicating with a source of gas to provide a flow of gas through said restricted passage in the direction of the axis of said opening,
means conducting a liquid to the exterior of said helical spring whereby the liquid may flow through the interstices between turns of said helical spring to provide a nebulizing fluid within said restricted passage;
wherein said helical spring defines an outlet having such small diameter that the nebulizing fluid fills the restricted passage in the absence of gas flow through the restricted passage.

* * * * *